United States Patent
Grases Freixedas et al.

(10) Patent No.: US 11,207,365 B2
(45) Date of Patent: Dec. 28, 2021

(54) COMBINED PREPARATIONS OF URINARY ACIDIFIERS AND CRYSTALLIZATION INHIBITORS AND APPLICATION THEREOF FOR THE TREATMENT OR PREVENTION OF PHOSPHATIC OR CALCIUM PHOSPHATE-INDUCED RENAL LITHIASIS

(71) Applicant: UNIVERSITAT DE LES ILLES BALEARS, Palma de Mallorca (ES)

(72) Inventors: Félix Grases Freixedas, Palma de Mallorca (ES); Antonia Costa Bauzá, Palma de Mallorca (ES); Rafael María Prieto Almirall, Palma de Mallorca (ES); Adrián Rodríguez Rodríguez, Palma de Mallorca (ES)

(73) Assignee: UNIVERSITAT DE LES ILLES BALEARS, Palma de Mallorca (ES)

( * ) Notice: Subject to any disclaimer, the term of this patent is extended or adjusted under 35 U.S.C. 154(b) by 0 days.

(21) Appl. No.: 16/257,113

(22) Filed: Jan. 25, 2019

(65) Prior Publication Data

US 2019/0216873 A1 Jul. 18, 2019

Related U.S. Application Data

(62) Division of application No. 15/300,486, filed as application No. PCT/ES2015/070249 on Mar. 31, 2015, now abandoned.

(30) Foreign Application Priority Data

Apr. 2, 2014 (ES) ................................ ES201430479

(51) Int. Cl.
| | |
|---|---|
| *A61K 36/45* | (2006.01) |
| *A61K 45/06* | (2006.01) |
| *A61K 31/198* | (2006.01) |
| *A61K 31/6615* | (2006.01) |
| *A61K 33/02* | (2006.01) |
| *A23L 2/00* | (2006.01) |
| *A23L 2/70* | (2006.01) |
| *A23L 33/175* | (2016.01) |

(52) U.S. Cl.
CPC ............... *A61K 36/45* (2013.01); *A23L 2/00* (2013.01); *A23L 2/70* (2013.01); *A23L 33/175* (2016.08); *A61K 31/198* (2013.01); *A61K 31/6615* (2013.01); *A61K 33/02* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,849,452 A | 7/1989 | Dulce et al. | |
| 4,902,718 A * | 2/1990 | Bayless | A61K 31/195 514/562 |
| 9,895,396 B2 * | 2/2018 | Goldfarb | A61K 31/194 |

FOREIGN PATENT DOCUMENTS

| | | |
|---|---|---|
| CN | 103204874 A | 7/2013 |
| EP | 0344997 A2 | 12/1989 |
| GB | 520248 A | 4/1940 |
| JP | 61109730 A * | 5/1986 |
| JP | S63284108 A | 11/1988 |
| WO | 9732565 A1 | 9/1997 |
| WO | 2007004244 A2 | 1/2007 |

OTHER PUBLICATIONS

Grases et al. "Renal stone formation and development." International Urology and Nephrology 31.5 (1999): 591-600.
Grases et al. "Phytate acts as an inhibitor in formation of renal calculi." Front Biosci 12.1 (2007): 2580-7.
McHarg et al. "Influence of cranberry juice on the urinary risk factors for calcium oxalate kidney stone formation." BJU international 92.7 (2003): 765-768.
Pragasam et al. "Oral I-arginine supplementation ameliorates urinary risk factors and kinetic modulation of Tamm-Horsfall glycoprotein in experimental hyperoxaluric rats." Clinica Chimica Acta 360.1-2 (2005): 141-150.
Reveillaud et al. "Les lithiases urinaires médicamenteuses. [Drug-induced urinary calculi]." La Presse médicale 12.38 (1983): 2389-2392.
Selvam. "Calcium oxalate stone disease: role of lipid peroxidation and antioxidants." Urological research 30.1 (2002): 35-47.
International Search Report and Written Opinion in corresponding International Patent Application No. PCT/ES2015/070249 dated Jun. 18, 2015. 14 pages.
International Preliminary Report on Patentability in corresponding International Patent Application No. PCT/ES2015/070249 dated Oct. 4, 2016. 9 pages.
European Examination Report in corresponding European Patent Application No. 15717192.7 dated Dec. 13, 2017. 9 pages.

* cited by examiner

*Primary Examiner* — Susan Hoffman
(74) *Attorney, Agent, or Firm* — Leason Ellis LLP

(57) ABSTRACT

The present invention is related to the use of a separate, sequential or simultaneous combination of at least one urinary acidifier with at least one calcium phosphate crystallization inhibitor for urine acidification, and thus preventing the pH at which supersaturation of calcium phosphate is produced and consequently, renal lithiasis.

8 Claims, 1 Drawing Sheet

COMBINED PREPARATIONS OF URINARY ACIDIFIERS AND CRYSTALLIZATION INHIBITORS AND APPLICATION THEREOF FOR THE TREATMENT OR PREVENTION OF PHOSPHATIC OR CALCIUM PHOSPHATE-INDUCED RENAL LITHIASIS

CROSS-REFERENCE TO RELATED PATENT APPLICATIONS

This application is a divisional of U.S. patent application Ser. No. 15/300,486 filed Sep. 29, 2016, now abandoned, which was a U.S. National Stage Application under 35 U.S.C. § 371 of International Patent Application No. PCT/ES2015/070249 filed Mar. 31, 2015, which claims the benefit of priority under 35 U.S.C. Section 119€ of Spanish Patent Application number P201430479 filed Apr. 2, 2014, all of which are incorporated by reference in their entireties.

DESCRIPTION

The present invention is related to the use of a separate, sequential or simultaneous combination of at least one urinary acidifier with at least one calcium phosphate crystallization inhibitor for urine acidification, and thus preventing the pH at which supersaturation of calcium phosphate and consequently, renal lithiasis is produced.

STATE OF THE ART

Urine acidification is not an easy task and today it is known that substances such as ammonium chloride or arginine, in amounts on the order of 1 g/day, are able to reduce urinary pH values. This is because they act as carriers of hydrogen ions to the nephron, where they are released and thereby acidify the urine. The main problem of the continued use of these products is that when consumed during very long periods of time they are no longer effective. It is also known that eating berries such as blueberries achieves a significant acidification of urine, with the advantage that this effect is maintained even when their consumption is prolonged in time. The precise mechanism of the acidification process is not known, although some components of this fruit to which this acidifying capacity can be attributed have been identified (Raz R, Chazan B, Dan M. Cranberry Juice and Urinary Tract Infection. Clin Infect Dis 2004; 38(10): 1413-1419).

It is now known that for urinary pH values higher than 6.2 human urine is always supersaturated with respect to calcium phosphate, that can crystallize as brushite (kinetically favorable form) or hydroxyapatite (thermodynamically stable form). These high urinary pH values sometimes are associated with the consumption of strictly vegetarian diets, excessive intake of carbonated beverages or consumption of antacids. For this reason, changing these habits can sometimes be enough to prevent these high urinary pH values, although unfortunately in many cases it is not achieved. On the other hand, there is also an alteration of the mechanism of hydrogen ions excretion at the nephron level, known as renal tubular acidosis, which prevents acidifying urine which is why the urine pH of these individuals is permanently higher than 6 and, in these cases, all procedures intended to acidify it fail (Rodriguez Soriano J. Renal tubular acidosis: the clinical entity. J Am Soc Nephrol 2002; 13: 2160-2170).

The formation of calcium phosphate crystals in supersaturated urines, that is, for pH values higher than 6.2, also depends on the presence of crystallization inhibitors. In this case, several substances with this capability have been described among which it is worth noting citrate, pyrophosphate and phytate (16-18). Of these, only citrate and phytate can be administered orally since pyrophosphate is hydrolyzed in the stomach and therefore it is not absorbed as such (Grases F, Ramis M, Costa-Bauzá A. Effects of phytate and pyrophosphate on brushite and hydroxyapatite crystallization. Comparison with the action of other polyphosphates. Urol Res 2000; 28: 136-140). Citrate, in addition to being a crystallization inhibitor, is a very effective urinary basifying, therefore, except for patients with renal tubular acidosis, which has a specific treatment, since urine pH cannot be reduced, it will not be suitable for patients whose problem is attributed to high levels of urinary pH. Therefore, out of the crystallization inhibitors that can currently be delivered orally, the only remaining one is phytate. It is known that the ionic species of phytic acid (phytates) have the capacity to inhibit the development of calcium salts in biological fluids, decreasing the risk of both developing calcium kidney stones (Grases F, Isern B, Sanchis P, Perello J, Torres J J, Costa-Bauza A. Phytate acts as an inhibitor in formation of renal calculi. Front Biosci 2007; 12: 2580-2587), and developing other pathological calcifications (Grases F, Sanchis P, Perello J, Isern B, Prieto R M, Fernandez Palomeque C, Torres J J. Effect of crystallization inhibitors on vascular calcifications induced by Vitamin D. A pilot study in Sprague-Dawley rats. Circ J 2007; 71(7): 1152-1156). It is also known that phytate, which is found in tissues and fluids of mammals, comes mainly from the diet.

Noninfectious phosphatic renal lithiasis may also be associated in some occasions with hypercalciuria. Prophylactic treatment of this lithiasis is based primarily on implementing dietary measures to decrease the urinary pH. For this reason, it is recommended to reduce the excessive consumption of vegetables, avoid citrus, avoid carbonated beverages and antacids, increase the intake of animal protein and consume blueberries. If it is also associated with hypercalciuria, it must be properly treated depending on the type of hypercalciuria.

The presence of calcium phosphate crystals in the urine, in addition to being linked to the genesis of phosphate stones, can induce the development of calcium oxalate stones (apparently 'pure') through heterogeneous nucleation mechanisms and formation of mixed calcium oxalate/calcium phosphate renal stones Therefore there is a need to be able to decrease in an effective and controlled manner the pH of urine to prevent supersaturation of calcium phosphate and, with it, lithiasis.

DESCRIPTION OF THE INVENTION

The present invention provides a method for the treatment and prevention of calcium phosphate or calcium oxalate stones induced by calcium phosphate by the combined use of urinary acidifiers and crystallization inhibitors of calcium salts. The combination of these two types of compounds produces a synergistic effect, which is able to increase the time it takes for calcium phosphate to precipitate, the first stage in the formation of kidney stones.

It can be concluded that, as evidenced by the provided experimental evidence, for the same amount of inhibitor, there is a significant increase in its inhibitory capacity by decreasing the pH of the medium, a fact unknown to date and that demonstrates a synergistic effect between urinary acidification and inhibition of crystallization. Taking this effect into account, in order to prevent formation of calcium phosphate salts, urine acidifiers can be administered simultaneously or sequentially, separately or in a single composition together with crystallization inhibitors of calcium salts to a patient.

Therefore, in a first aspect the present invention is related to the use of a preparation comprising at least one urinary acidifier combined sequentially, simultaneously or separately with at least one inhibitor of calcium phosphate crystallization, in the manufacture of a medicament.

Another aspect of the invention is related to the use of a preparation comprising at least one urinary acidifier combined sequentially, simultaneously or separately with at least one calcium phosphate crystallization inhibitor, in the manufacture of a medicament for the treatment or prevention of renal lithiasis.

The term urinary acidifiers is referred to all those substances currently known which when supplied orally, decrease urinary pH values. Among the most known and used today are blueberries (in powdered form, extract, or dried form), ammonium chloride and arginine chloride. The doses used of ammonium chloride and arginine chloride go from 200 mg/day to 3000 mg/day.

The term 'renal lithiasis', 'urolithiasis' or 'nephrolithiasis' is referred to the disorder caused by the presence of stones inside the kidneys or the urinary tract (ureters, bladder). Kidney stones are made up of substances that are normal in urine (calcium salts, uric acid, cystine etc.) which for various reasons have concentrated and precipitated forming fragments of larger or smaller size.

The term 'calcium phosphate crystals' or 'calcium phosphate stones' includes all that process or conditions that imply/induce the formation of solid precipitates in the urine in which this substance is involved.

In a preferred embodiment, the urinary acidifier is selected from a portion or an extract of the plant species *Vaccinum*, pharmaceutically acceptable ammonium salts, arginine or any of its pharmaceutically acceptable salts, cysteine or any of its pharmaceutically acceptable salts, phenazopyridine or any of its pharmaceutically acceptable salts, or mixtures thereof.

In a more preferred embodiment, the urinary acidifier is selected from cranberry, ammonium chloride, L-arginine, L-cysteine or mixtures thereof.

In another preferred embodiment, the crystallization inhibitor is phytic acid or any of its pharmaceutically acceptable salts.

In the present invention, 'phytate' or 'myo-inositol-hexaphosphate' is understood as the molecule of the formula:

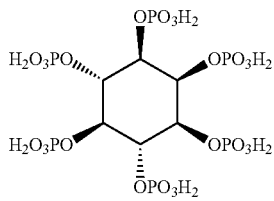

and its pharmaceutically acceptable salts, which include but are not limited to sodium, potassium, calcium, magnesium, zinc and calcium-magnesium salts. For the purposes of the present invention, phytic acid and/or its pharmaceutically acceptable salts may be used in free form as pure substances, extracts of plant species containing them, such as, for example, extracts of brown rice, or carried by plant species containing them, such as the germs or the external parts of wheat, oat, soy, almond, locust bean, etc. grains or fruits.

In a preferred embodiment, the pharmaceutically acceptable salts of phytic acid are selected from sodium phytate, potassium phytate, calcium phytate, magnesium phytate, zinc phytate, calcium-magnesium phytate or combinations of the same.

In a more preferred embodiment, the phytic acid or its salts are derived from a portion of a plant species rich in phytic acid or its salts, or from a plant extract of said species.

In another preferred embodiment, the medicament is in a form suitable for oral, parenteral, enteral or intravenous administration.

In another preferred embodiment, it is calcium phosphate-induced calcium oxalate renal lithiasis.

In another preferred embodiment, renal lithiasis is a mix of calcium oxalate/calcium phosphate, induced by calcium phosphate.

Another aspect of the invention is referred to a composition comprising at least one urinary acidifier and at least one calcium phosphate crystallization inhibitor.

In a preferred embodiment, the urinary acidifier included in the composition is selected from a portion or an extract of the plant species *Vaccinum*, pharmaceutically acceptable ammonium salts, arginine or any of its pharmaceutically acceptable salts, cysteine or any of its pharmaceutically acceptable salts, phenazopyridine or any of its pharmaceutically acceptable salts, methionine or any of its pharmaceutically acceptable salts or mixtures thereof.

In a more preferred embodiment, the urinary acidifier included in the composition is selected from cranberry, ammonium chloride, L-arginine, L-cysteine or mixtures thereof.

In another preferred embodiment, the crystallization inhibitor included in the composition is phytic acid or any of its pharmaceutically acceptable salts.

In a more preferred embodiment, the pharmaceutically acceptable salts of phytic acid included in the composition are selected from sodium phytate, potassium phytate, calcium phytate, magnesium phytate, zinc phytate and calcium-magnesium phytate.

In another preferred embodiment, the phytic acid or its salts included in the composition are derived from a portion of a plant species rich in phytic acid or its salts, or from a plant extract of said plant species.

In another preferred embodiment, the composition of the invention comprises between 20-40% by weight of a urinary acidifier and between 15-30% by weight of the crystallization inhibitor. Non-limiting examples of the composition of the invention are the following:

| Composition 1 | |
|---|---|
| Compound | Amount |
| American cranberry | 200 mg |
| L-arginine | 180 mg |
| L-cysteine | 180 mg |
| Calcium magnesium phytate (phytin) | 120 mg |

| Composition 2 | |
|---|---|
| Compound | Amount |
| American cranberry | 250 mg |
| L-arginine | 150 mg |

-continued

Composition 2

| Compound | Amount |
| --- | --- |
| L-cysteine | 150 mg |
| Calcium magnesium phytate (phytin) | 150 mg |

Composition 3

| Compound | Amount |
| --- | --- |
| American cranberry | 220 mg |
| L-arginine | 160 mg |
| L-cysteine | 160 mg |
| Calcium magnesium phytate (phytin) | 180 mg |

Composition 4

| Compound | Amount |
| --- | --- |
| American cranberry | 230 mg |
| L-arginine | 130 mg |
| L-cysteine | 130 mg |
| Potassium phytate | 130 mg |

In another preferred embodiment, the composition is a pharmaceutical composition or a nutraceutical or functional food.

In the present invention 'nutraceutical' or 'functional food' is understood as a food that has a beneficial effect on health. In the same way, the term nutraceutical can be applied to extracts or chemical compounds derived from common foods. Examples of foods that are attributed the nutraceutical properties are olive oil, red wine, broccoli, soy, etc. Nutraceuticals are normally used in nutritional mixtures and in the pharmaceutical industry. In the same way as some foods may be classified as nutraceuticals, some nutritional supplements are also classified as that, such as, for example, fatty acids such as omega-3 derived from fish oil and some vegetables or antioxidants and vitamins.

Another aspect of the invention is related to the use of the composition described above in the preparation of a medicament.

Another aspect of the invention is related to the use of the composition described above for the treatment and/or prevention of renal lithiasis.

Another aspect of the invention is related to a kit comprising at least one urinary acidifier and at least one calcium phosphate crystallization inhibitor.

In a preferred embodiment, the urinary acidifier included in the kit is selected from a portion or an extract of the plant species *Vaccinum*, pharmaceutically acceptable ammonium salts, arginine or any of its pharmaceutically acceptable salts, cysteine or any of its pharmaceutically acceptable salts, phenazopyridine or any of its pharmaceutically acceptable salts, In another preferred embodiment, the urinary acidifier included in the kit is selected from cranberry, ammonium chloride, L-arginine, L-cysteine or mixtures thereof.

In another preferred embodiment, the crystallization inhibitor included in the kit is phytic acid or any of its pharmaceutically acceptable salts.

In a more preferred embodiment, the pharmaceutically acceptable salts of phytic acid included in the kit are selected from sodium phytate, potassium phytate, calcium phytate, magnesium phytate, zinc phytate and calcium-magnesium phytate.

In another preferred embodiment, phytic acid or its salts are derived from a portion of a plant species rich in phytic acid or its salts, or from a plant extract of said plant species.

Another aspect of the invention is referred to the composition described above for use in the treatment or prevention of renal lithiasis.

Another aspect of the invention is referred to a method for the treatment or prevention of renal lithiasis comprising the simultaneous or sequential administration of at least one urinary acidifier and of at least one calcium phosphate crystallization inhibitor, either separately or together in the same composition, to an individual in need thereof.

The combination of urinary acidifying agents and calcium phosphate crystallization inhibitors may be administrated in solid form (including granules, powders or suppositories) or in liquid form (such as solutions, suspensions or emulsions). In turn, they may be administered as such or after being subjected to operations such as sterilization, addition of preservatives, addition of stabilizers or addition of emulsifiers.

The co-administration of urinary acidifying agents and calcium phosphate crystallization inhibitors may be combined with one or more compounds, which facilitate absorption thereof through the route of administration selected. Thus, they can be administered with lactose, sucrose, talc, magnesium stearate, cellulose, calcium salts, gelatin, fatty acids, as well as with other similar substances.

The pharmaceutically acceptable adjuvants and vehicles that may be used in said compositions are the adjuvants and vehicles known by the persons skilled in the art and commonly used in the preparation of therapeutic compositions.

For application in therapy, the urinary acidifiers and the calcium phosphate crystallization inhibitors will be, preferably, in a pharmaceutically acceptable or substantially pure form, that is, having a level of pharmaceutically acceptable purity excluding the normal pharmaceutical additives such as diluents and carriers, and including no material considered toxic at normal dosage levels. The purity levels for the active principle are preferably higher than 50%, more preferably higher than 70%, and still more preferably higher than 90%. In a preferred embodiment, they are higher than 95% of compound of formula (I), or salts or solvates thereof.

Throughout the description and the claims the word 'comprises' and its variants are not intended to exclude other technical features, additives, components or steps. For those skilled in the art, other objects, advantages and features of the invention will become apparent in part from the description and in part from the practice of the invention. The following examples and figure are provided by way of illustration, and are not intended to be limiting of the present invention.

EXAMPLES

Next, the invention will be illustrated by means of tests performed by the inventors that reveal the effectiveness of the product of the invention.

Example 1: Measurement of the Times of Crystallization of Calcium Phosphate

Figure 1:
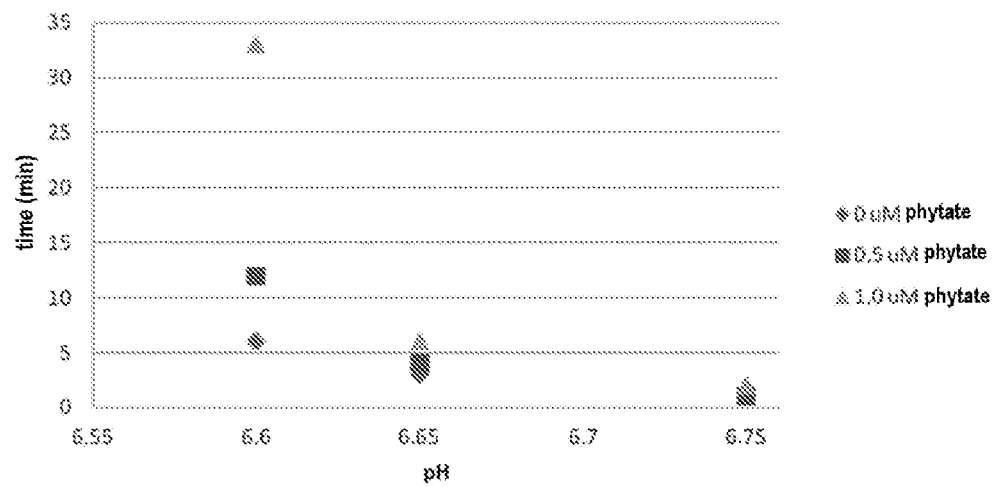
FIG. 1. It shows the graphical representation of the induction times (in minutes) for a 15 mM phosphate and 3 mM calcium solution, in artificial urine, at different pH and phytate concentration.
Figure 2:
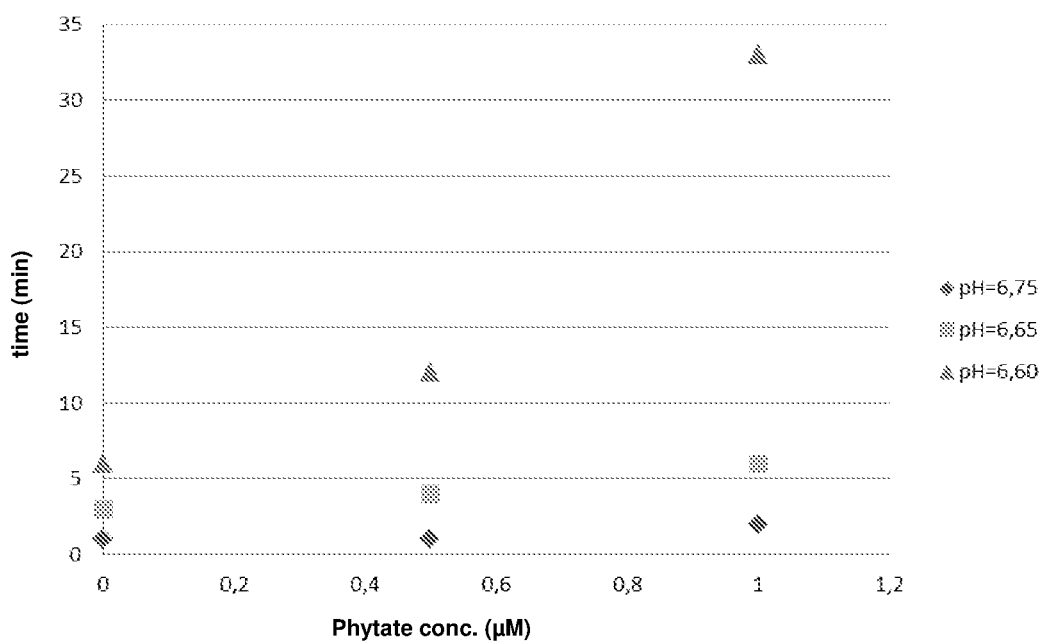
FIG. 2. It shows the graphical representation of the induction times (in minutes) against a phytate concentration ($\mu M$), according to the pH.

From a 15 mM phosphate ion and 3 mM calcium ion solution in artificial urine, the induction times for the crystallization of calcium phosphate have been calculated at different pH and phytate concentration. The artificial urine had no magnesium since it is shown that the magnesium ion is a calcium phosphate crystallization inhibitor. Table 1 shows said induction times, which as it can be clearly seen (FIG. 1) increase with the decrease of the pH and with the increase of the phytate concentration. Thus, while at pH 6.75, the calcium phosphate solution (without inhibitor) takes 1 minute to crystallize, with 1 µM phytate it takes 2 minutes (the delay in the induction time at this pH value is 1 minute, for 1 µM phytate). However, when the pH decreases to 6.60, the calcium phosphate solution (without inhibitor) takes 6 minutes to crystallize, while with 1 µM phytate it takes 33 minutes (the delay in the induction time at this pH value is 27 minutes, for 1 µM phytate). Thus, for the same amount of inhibitor there is a significant increase of the crystallization time when the value of the pH of the solution decreases.

TABLE 1 induction times (in minutes) for a 15 mM phosphate and 3 mM calcium solution, in artificial urine, at different pH and phytate concentration.

| | t (min) pH = 6.75 | t (min) pH = 6.65 | t (min) pH = 6.60 |
|---|---|---|---|
| 0 µM phytate | 1 | 3 | 6 |
| 0.5 µM phytate | 1 | 4 | 12 |
| 1.0 µM phytate | 2 | 6 | 33 |

The invention claimed is:

1. A method of treating and/or preventing renal lithiasis in a subject comprising administering to the subject a composition comprising at least one urinary acidifier combined with at least one calcium phosphate crystallization inhibitor, wherein the urinary acidifier is one or more of: (i) a portion or an extract of a plant species *Vaccinum* or its pharmaceutically acceptable ammonium salts; (ii) arginine or its pharmaceutically acceptable salts; (iii) cysteine or its pharmaceutically acceptable salts; (iv) methionine or its pharmaceutically acceptable salts, wherein the crystallization inhibitor is phytic acid or its pharmaceutically acceptable salts, wherein the renal lithiasis is: (i) phosphatic lithiasis, (ii) calcium phosphate lithiasis, (iii) calcium oxalate lithiasis induced by calcium phosphate; or (iv) a mixed calcium oxalate/calcium phosphate lithiasis induced by calcium phosphate, wherein the combination of the at least one urinary acidifier and the phytic acid or its pharmaceutically acceptable salts exhibits a synergistic effect for improving inhibition of crystallization of calcium phosphate.

2. The method according to claim 1, wherein the urinary acidifier is methionine.

3. The method according to claim 1, wherein the pharmaceutically acceptable salts of phytic acid are selected from sodium phytate, potassium phytate, calcium phytate, magnesium phytate, zinc phytate, calcium-magnesium phytate or combinations thereof.

4. The method according to claim 3, wherein the pharmaceutically acceptable salt of phytic acid is calcium-magnesium phytate.

5. The method according to claim 1, wherein phytic acid or its salts are derived from a portion of a plant species containing phytic acid or its salts, or from a plant extract of said plant species.

6. The method according to claim 1, wherein the composition is suitable for oral, parenteral, enteral or intravenous administration.

7. The method according to claim 1, wherein the composition is a pharmaceutical composition, a nutraceutical or a functional food.

8. The method according to claim 1, wherein the composition comprises between 15-30% by weight of the crystallization inhibitor.

* * * * *